United States Patent
Chang et al.

(10) Patent No.: US 11,737,218 B2
(45) Date of Patent: Aug. 22, 2023

(54) HEAD-MOUNTED DISPLAY DEVICE

(71) Applicant: HTC Corporation, Taoyuan (TW)

(72) Inventors: Li-Hsun Chang, Taoyuan (TW);
Tian-Jia Hsieh, Taoyuan (TW);
Chih-Hsiang Hsieh, Taoyuan (TW);
Chen-Fu Chang, Taoyuan (TW)

(73) Assignee: HTC Corporation, Taoyuan (TW)

( * ) Notice: Subject to any disclaimer, the term of this patent is extended or adjusted under 35 U.S.C. 154(b) by 0 days.

(21) Appl. No.: 17/143,173

(22) Filed: Jan. 7, 2021

(65) Prior Publication Data
US 2021/0385954 A1 Dec. 9, 2021

Related U.S. Application Data

(60) Provisional application No. 63/036,451, filed on Jun. 9, 2020.

(51) Int. Cl.
*H05K 5/00* (2006.01)
*H05K 5/02* (2006.01)
(Continued)

(52) U.S. Cl.
CPC ....... *H05K 5/0017* (2013.01); *G02B 27/0176* (2013.01); *H05K 5/0086* (2013.01); *H05K 5/0217* (2013.01); *A61F 9/026* (2013.01); *A61F 9/028* (2013.01); *G02C 3/003* (2013.01); *G02C 11/08* (2013.01)

(58) Field of Classification Search
CPC .. H05K 5/0017; H05K 5/0086; H05K 5/0217; G02B 27/0176; A61F 9/026; A61F 9/028; G02C 3/003; G02C 11/08
See application file for complete search history.

(56) References Cited

U.S. PATENT DOCUMENTS

| 4,825,488 A | 5/1989 | Bedford |
| 6,409,338 B1 * | 6/2002 | Jewell ............ G02C 11/10 |
| | | 351/158 |

(Continued)

FOREIGN PATENT DOCUMENTS

| CN | 110771271 | 3/2021 |
| FR | 2944416 | 10/2010 |
| WO | 2014082023 | 5/2014 |

OTHER PUBLICATIONS

"Search Report of Europe Counterpart Application", dated Oct. 29, 2021, p. 1-p. 4.

(Continued)

*Primary Examiner* — Sahlu Okebato
(74) *Attorney, Agent, or Firm* — JCIPRNET

(57) ABSTRACT

A head-mounted display device includes a front assembly, a wearable assembly, and a cushion module. The wearable assembly is connected to the front assembly and is suitable for wearing the front assembly onto a face of a user. The cushion module includes a hard member, a soft member, and a fan. The hard member is connected to the wearable assembly. The soft member is connected to the hard member to contact skin of the user, and has a rear channel. The fan communicates with the rear channel. The soft member is connected to the hard member to contact the skin of the user, and the fan drives airflow to flow through the rear channel of the soft member to provide a heat dissipation effect.

13 Claims, 22 Drawing Sheets

(51) Int. Cl.
*G02B 27/01* (2006.01)
*G02C 11/08* (2006.01)
*A61F 9/02* (2006.01)
*G02C 3/00* (2006.01)

(56) References Cited

U.S. PATENT DOCUMENTS

| | | | |
|---|---|---|---|
| 2016/0255748 A1* | 9/2016 | Kim | G02B 27/017 |
| | | | 361/695 |
| 2018/0098465 A1* | 4/2018 | Reynolds | G02B 27/028 |
| 2020/0110449 A1* | 4/2020 | Chang | H05K 7/20172 |
| 2020/0246693 A1* | 8/2020 | Connor | G06F 1/163 |
| 2021/0185855 A1* | 6/2021 | Maric | G06F 3/011 |
| 2021/0325631 A1* | 10/2021 | Tao | G02B 25/001 |

OTHER PUBLICATIONS

"Office Action of Taiwan Counterpart Application", dated Oct. 29, 2021, p. 1-p. 5.
Office Action of European Counterpart Application, dated Nov. 11, 2021, pp. 1-7.
WOOLALA, "WOOLALA Cooling Seat Cushion with Fan, Cool Seat Cover Anti-Sweat Airflow Mattress Pad for Car, Office Chair, Wheelchair", available at "https://www.amazon.com/Cooling-Woolala-Anti-Sweat-Mattress-Wheelchair/dp/B07V2R9828".
"12V 3D Cooling Fan Front Car Seat Cushion Summer Air Cooler Chair Pad", available at "https://www.banggood.com/12V-3D-Cooling-Fan-Front-Car-Seat-Cushion-Summer-Air-Cooler-Chair-Pad-p-1441849.html?cur_warehouse=CN".

* cited by examiner

HEAD-MOUNTED DISPLAY DEVICE

CROSS-REFERENCE TO RELATED APPLICATION

This application claims the priority benefit of U.S. provisional application Ser. No. 63/036,451, filed on Jun. 9, 2020. The entirety of the above-mentioned patent application is hereby incorporated by reference herein and made a part of this specification.

BACKGROUND

Technical Field

The disclosure relates to a display device, and particularly, to a head-mounted display device.

Description of Related Art

With the development of the technology industry, the forms, functions, and usages of display devices are becoming more and more diversified, and a head-mounted display device that can be directly worn on the user has also been developed accordingly. There are many types of head-mounted display devices. Taking an eye-mask type head-mounted display device as an example, in addition to seeing the 3D image, the users will also see the 3D image changing as the users turn their heads after wearing this type of display device, which can provide the users with a more immersive experience.

The front assembly of the head-mounted display device is worn onto the user's face through the wearable assembly, so that the display module of the front assembly can project a display screen toward the user's eyes. In order to cushion the pressure exerted by the wearable assembly on the user's head, a cushion may be disposed between the wearable assembly and the user's head. However, the cushion tends to make the user feel stuffy after long-term use.

SUMMARY

The disclosure provides a head-mounted display device, and a cushion thereof has a proactive heat dissipation function.

A head-mounted display device of the present application includes a front assembly, a wearable assembly, and a cushion module. The wearable assembly is connected to the front assembly and is suitable for wearing the front assembly onto a face of a user. The cushion module includes a hard member, a soft member, and a fan. The hard member is connected to the wearable assembly. The soft member is connected to the hard member to contact skin of the user, and has a rear channel. The fan communicates with the rear channel.

Base on the above, the soft member is connected to the hard member to contact the skin of the user, and the fan drives airflow to flow through the rear channel of the soft member to provide a heat dissipation effect.

DESCRIPTION OF THE EMBODIMENTS

Figure 1A:
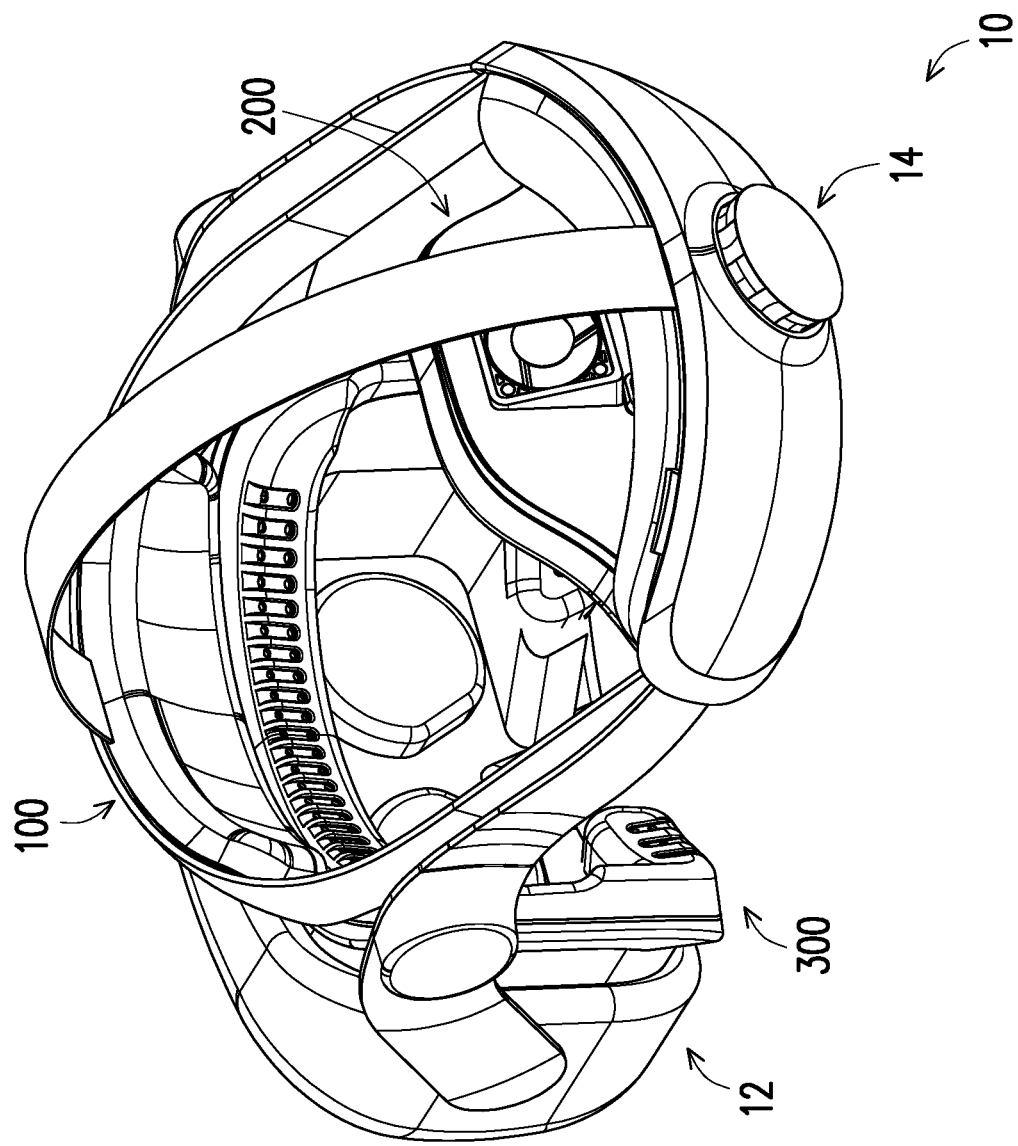
FIG. 1A is a perspective view of a head-mounted display device according to an embodiment of the invention.
Figure 1B:
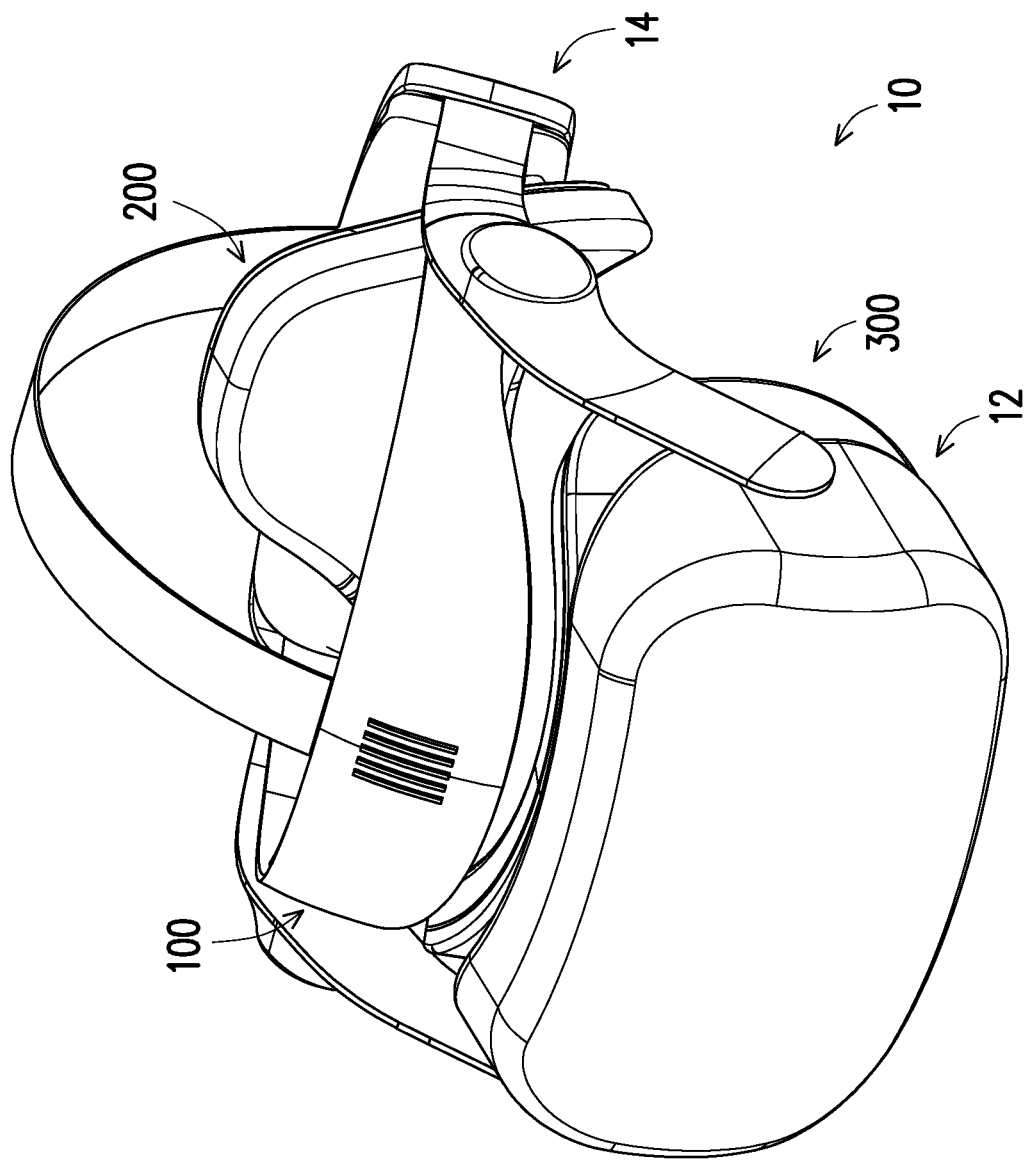
FIG. 1B is a perspective view of the head-mounted display device of FIG. 1A from another perspective.
Figure 2A:
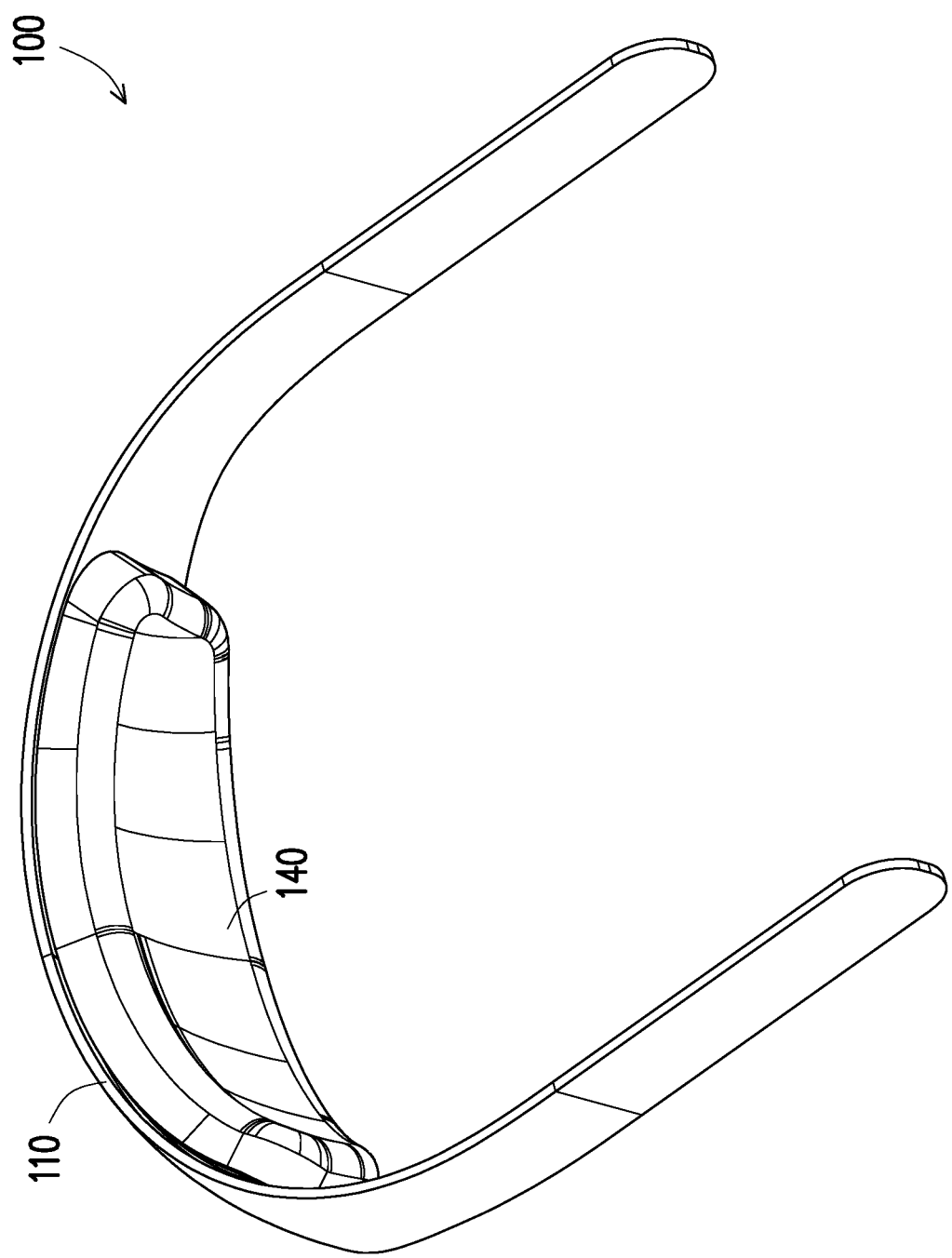
FIG. 2A is a perspective view of a first cushion module of FIG. 1A.
Figure 2B:
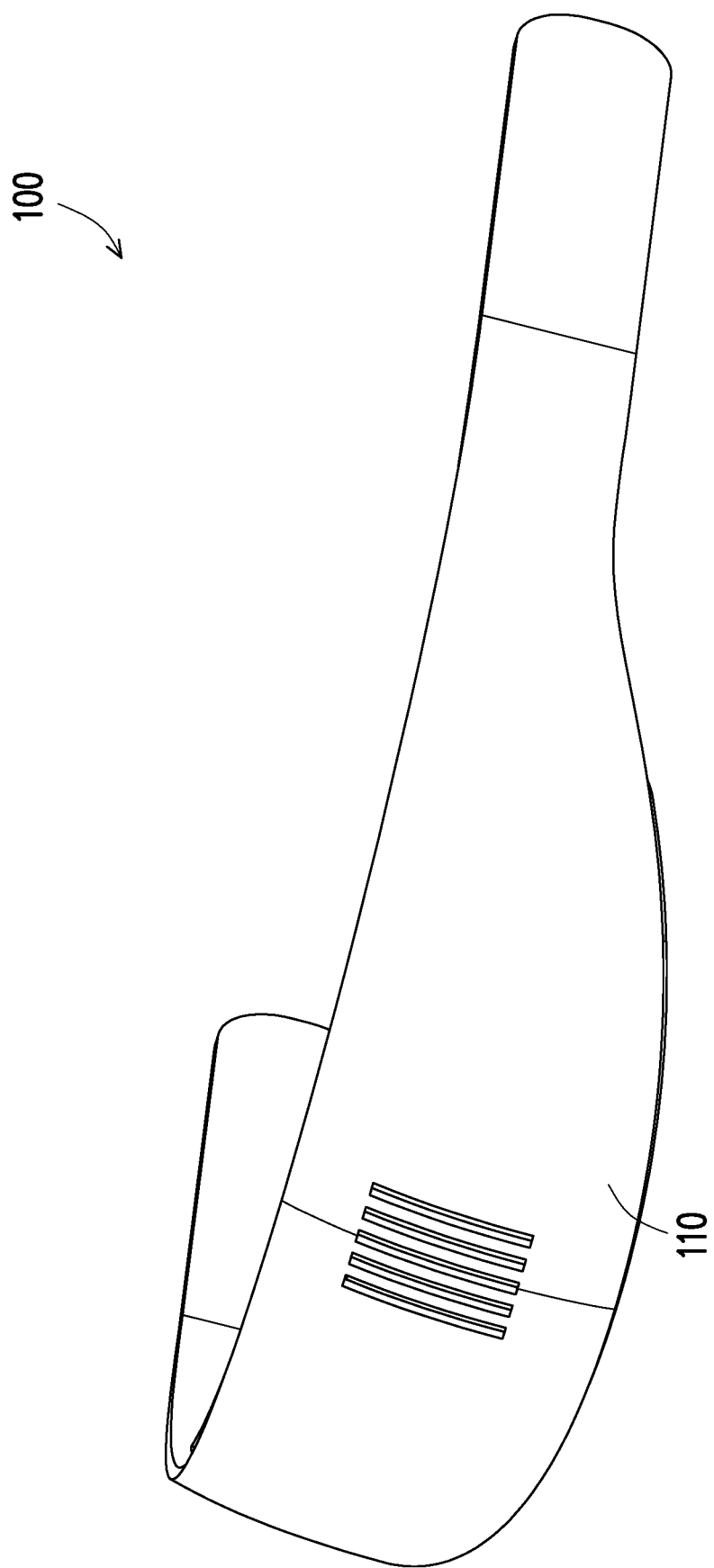
FIG. 2B is a perspective view of the first cushion module of FIG. 2A from another perspective.
Figure 3A:
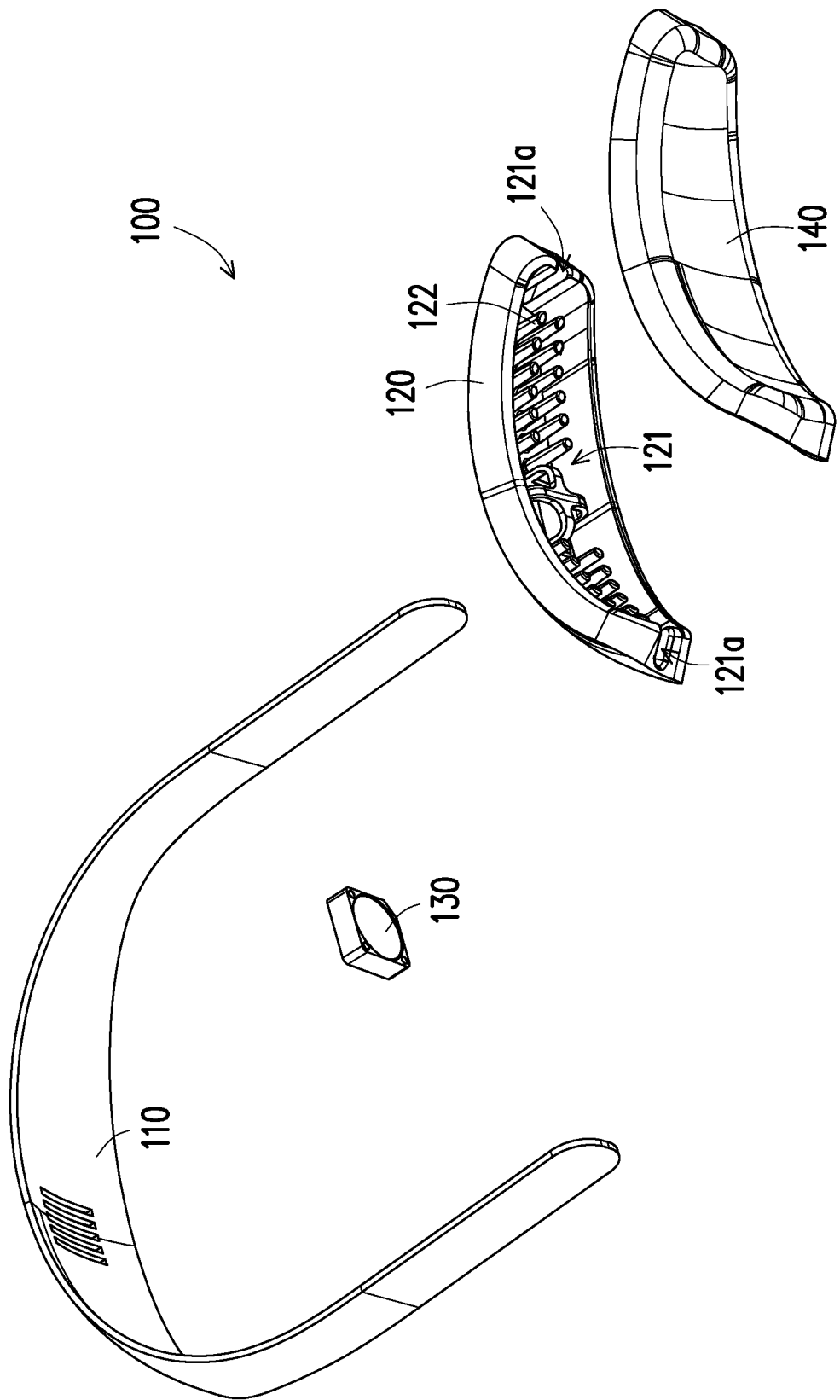
FIG. 3A is an exploded view of the first cushion module of FIG. 2A.
Figure 3B:
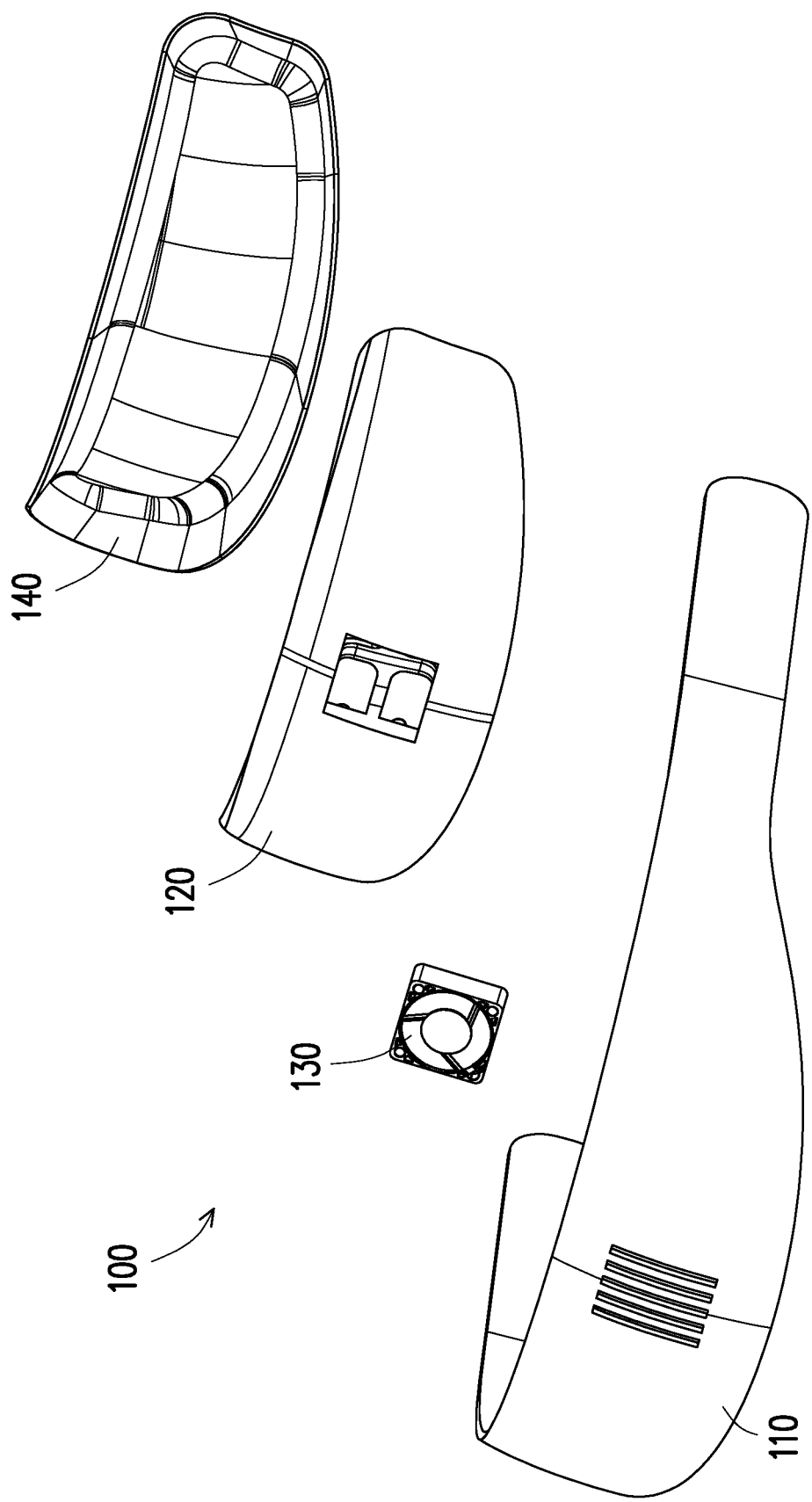
FIG. 3B is an exploded view of the first cushion module of FIG. 2A from another perspective.
Figure 4A:
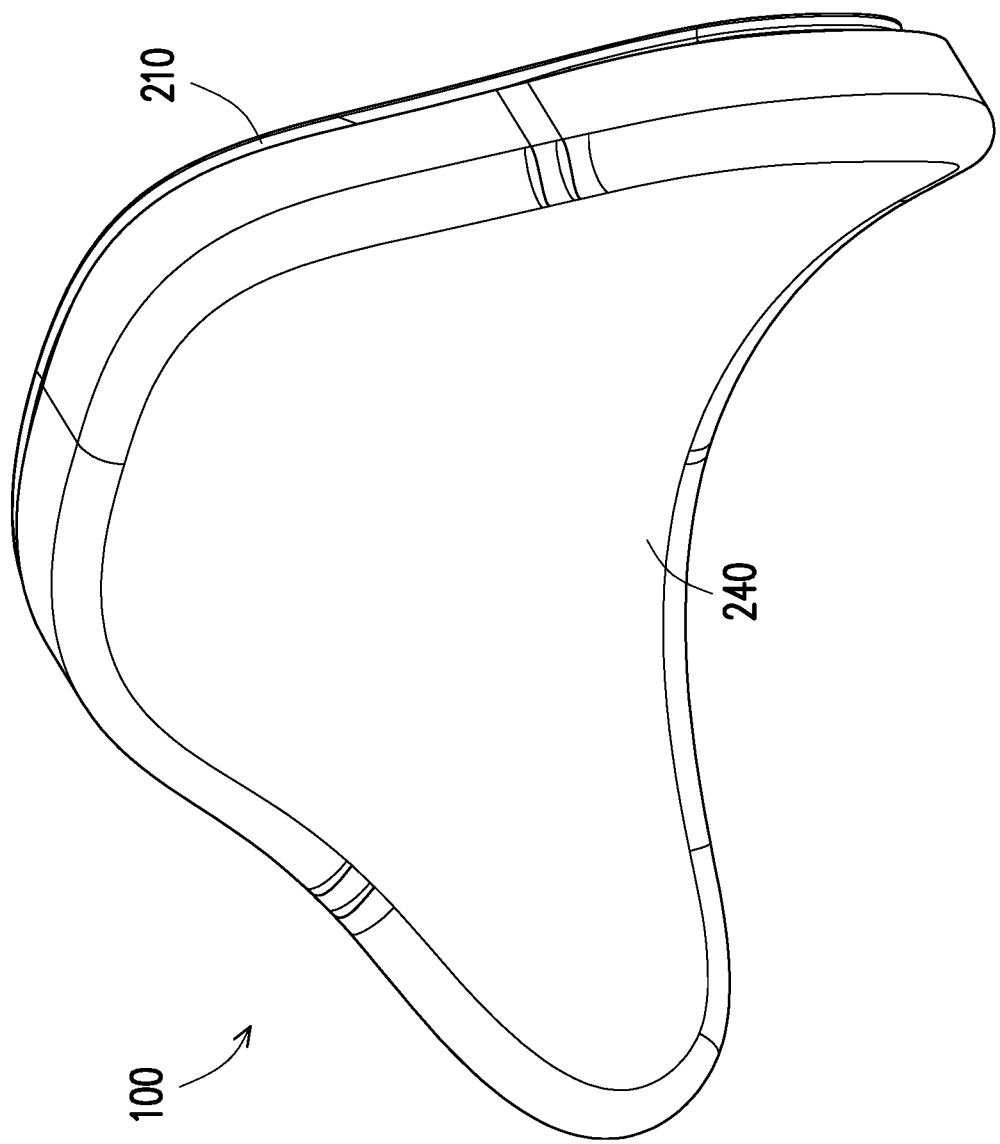
FIG. 4A is a perspective view of a second cushion module of FIG. 1A.
Figure 4B:
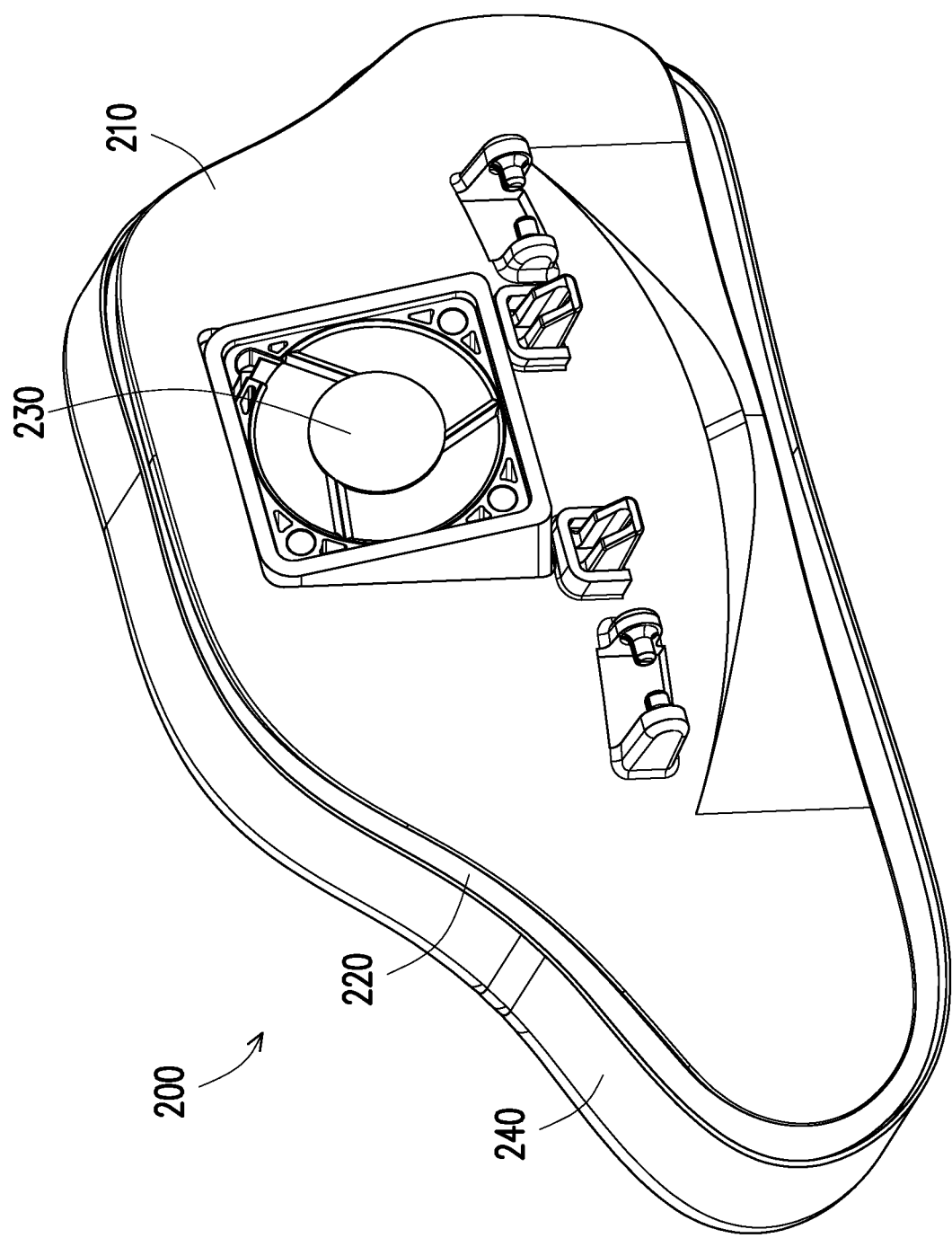
FIG. 4B is a perspective view of the second cushion module of FIG. 4A from another perspective.
Figure 5A:
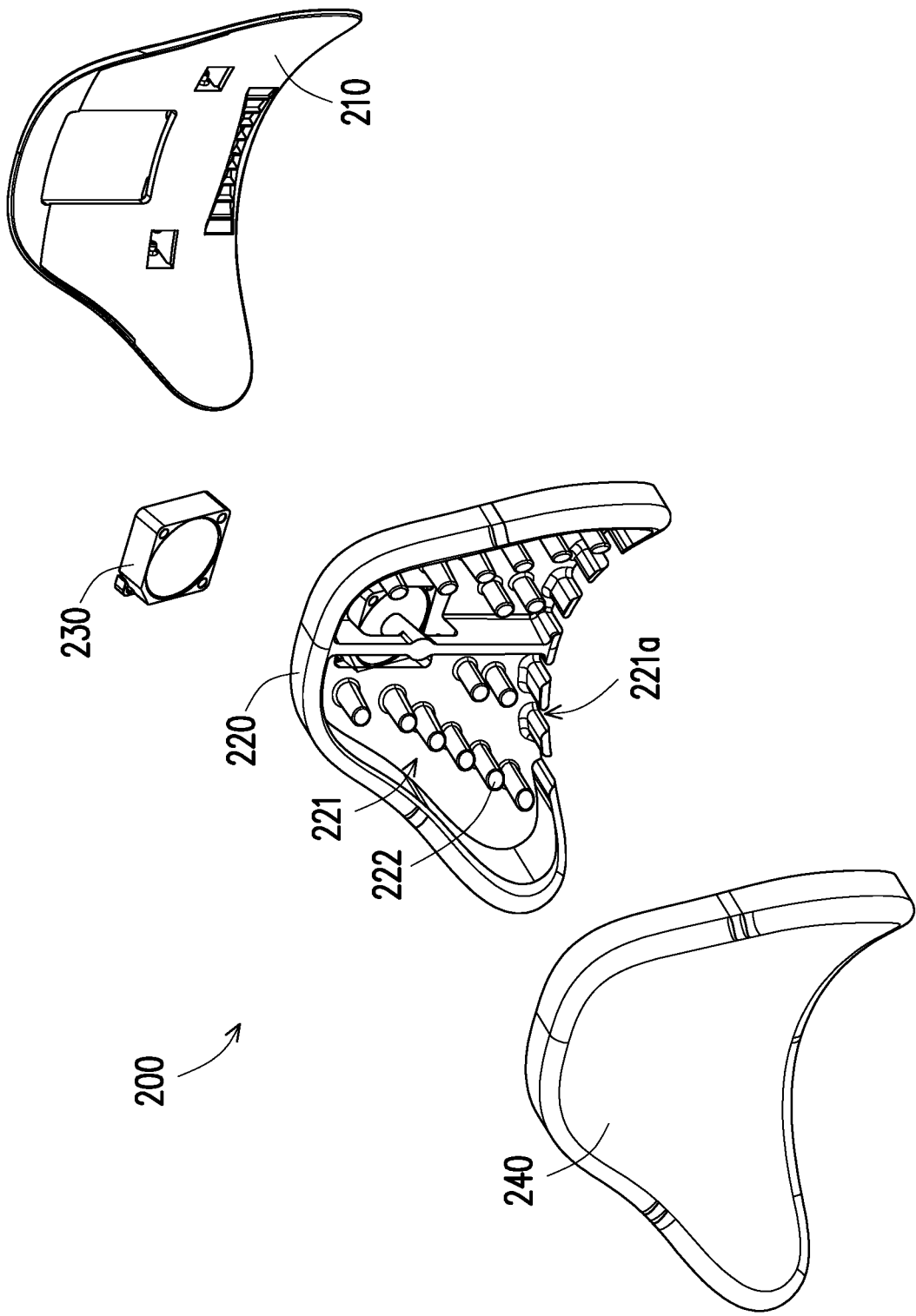
FIG. 5A is an exploded view of the second cushion module of FIG. 4A.
Figure 5B:
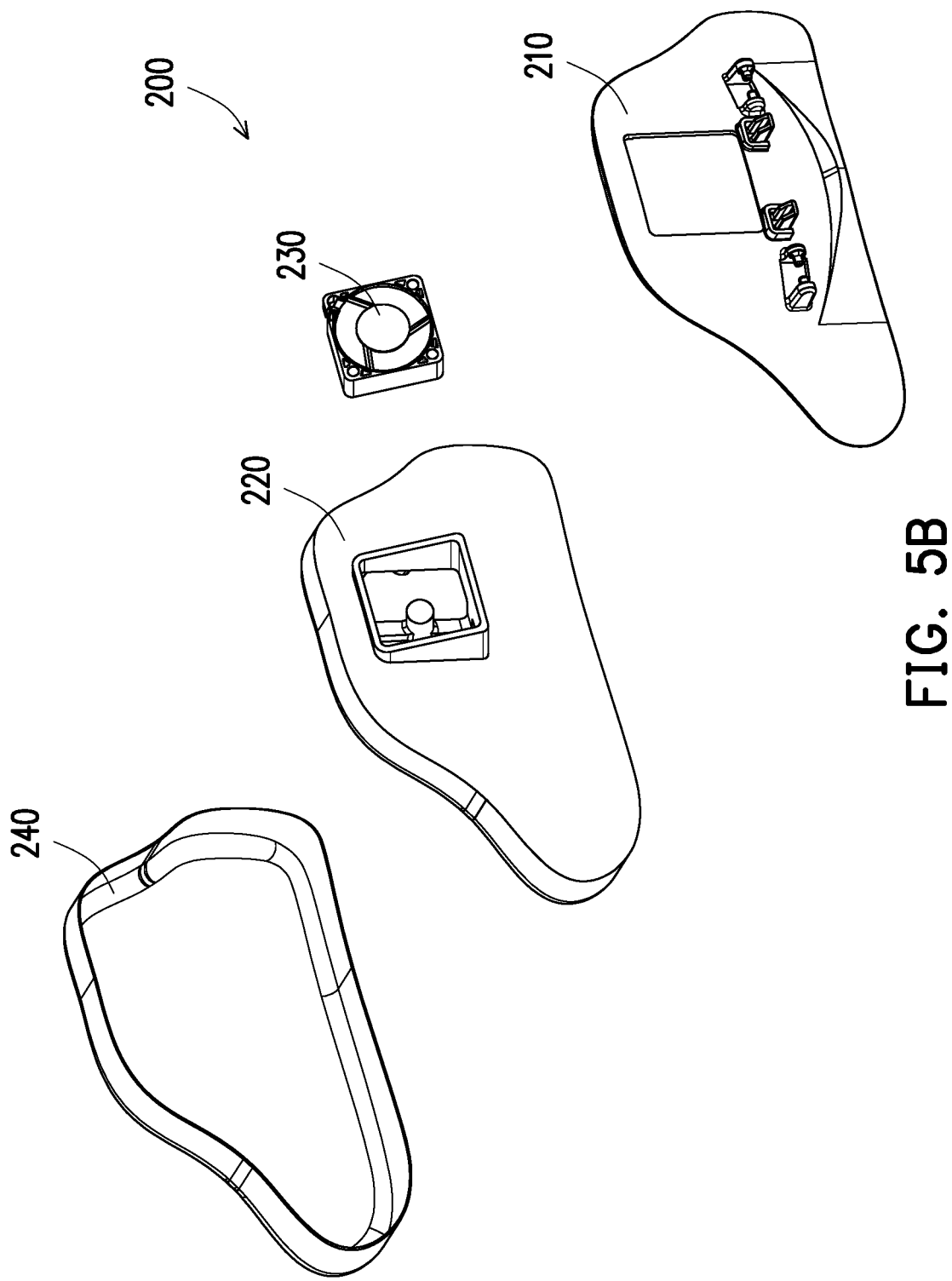
FIG. 5B is an exploded view of the second cushion module of FIG. 4A from another perspective.

Referring to FIGS. 1A and 1B, in this embodiment, a head-mounted display device 10 includes a front assembly 12 and a wearable assembly 14. The wearable assembly 14 is connected to the front assembly 12 and is suitable for wearing the front assembly 12 onto a face of a user.

In this embodiment, the front assembly 12 may include an optical system (not shown), a protective housing, and other elements, and may be provided with a display or suitable for being provided with the display. The display may be a built-in display or an additional portable display (such as a smart phone, etc.), but the present application is not limited thereto. A type of the display may be adjusted according to an application of the head-mounted display device 10 to a virtual reality system, an augmented reality system, or a mixed reality system. The optical system includes an optical member, such as a lens, a light guide member, or a prism, used to change an optical path of the display. In addition, the wearable assembly 14 may include any form of headband, and may also include any element or module used to adjust a length of the headband.

In order to cushion the pressure exerted by the wearable assembly 14 on a head of the user, the head-mounted display device 10 includes at least one of a first cushion module 100, a second cushion module 200, and a third cushion module 300. In this embodiment, the first cushion module 100 is used to abut against a frontal bone of the user. The second cushion module 200 is used to abut against an occipital bone of the user. The third cushion module 300 is used to abut against a face of the user, particularly around eye sockets of the user.

Referring to FIGS. 2A, 2B, 3A, and 3B, the first cushion module 100 may include a first hard member 110, a first soft member 120, and a first fan 130. The first hard member 110 is connected to the wearable assembly 14 (as shown in FIGS. 1A and 1B). The first soft member 120 is connected to the first hard member 110 to contact skin of the user, and has a first rear channel 121. The first fan 130 communicates with the first rear channel 121 to introduce external air into the first rear channel 121. The first fan 130 is, for example, an axial fan, but not limited thereto.

In this embodiment, a material of the first hard member 110 is, for example, plastic or other materials that are not easily compressed, to provide support. The first hard member 110 and a part of the wearable assembly 14 may be integrally formed.

In this embodiment, a material of the first soft member 120 is, for example, rubber, silicone, foam, or other materials that are easily compressed, to provide cushioning. The first soft member 120 may have multiple first pillars 122. The first pillars 122 may support the head of the user. The first rear channel 121 extends between the first pillars 122. The first soft member 120 has one or more first rear channel outlets 121a. The first rear channel outlets 121a communicate with the first rear channel 121 and are located on a surface of the first soft member 120 that does not contact the skin of the user. Since the airflow from the first fan 130 flows out of the first rear channel outlets 121a through the first rear channel 121 (that is, through the first pillars 122), the user is less likely to feel stuffy in an area where the first soft member 120 contacts the skin.

In this embodiment, the first cushion module 100 may further include a first fabric layer 140. The first fabric layer 140 covers the first soft member 120. The first fabric layer 140 may adopt a breathable and cool cloth. The first fabric layer 140 may cover the first soft member 120 in a detachable manner, to be removed for cleaning. In more detail, the airflow flowing in the first rear channel 121 facilitates evaporation of the sweat absorbed by the first fabric layer 140 so as to lower the temperature. Therefore, the user is less likely to feel stuffy in an area where the first fabric layer 140 contacts the skin.

Referring to FIGS. 4A, 4B, 5A, and 5B, the second cushion module 200 may include a second hard member 210, a second soft member 220, and a second fan 230. The second hard member 210 is connected to the wearable assembly 14 (as shown in FIGS. 1A and 1B). The second soft member 220 is connected to the second hard member 210 to contact the skin of the user, and has a second rear channel 221. The second fan 230 communicates with the second rear channel 221 to introduce the external air into the second rear channel 221. The second fan 230 is, for example, an axial fan, but not limited thereto.

In this embodiment, a material of the second hard member 210 is, for example, plastic or other materials that are not easily compressed, to provide support. The second hard member 210 and a part of the wearable assembly 14 may be integrally formed.

In this embodiment, a material of the second soft member 220 is, for example, rubber, silicone, foam, or other materials that are easily compressed, to provide cushioning. The second soft member 220 may have multiple second pillars 222. The second pillars 222 may support the head of the user. The second rear channel 221 extends between the second pillars 222. The second soft member 220 has one or more second rear channel outlets 221a. The second rear channel outlets 221a communicate with the second rear channel 221 and are located on a surface of the second soft member 220 that does not contact the skin of the user. Therefore, since the airflow of the second fan 230 flows out of the second rear channel outlets 221a through the second rear channel 221 (that is, through the second pillars 222), the user is less likely to feel stuffy in an area where the second soft member 220 contacts the skin.

In this embodiment, the second cushion module 200 may further include a second fabric layer 240. The second fabric layer 240 covers the second soft member 220. The second fabric layer 240 may adopt a breathable and cool cloth. The second fabric layer 240 may cover the second soft member 220 in a detachable manner, to be removed for cleaning. In more detail, the airflow flowing in the second rear channel 221 facilitates evaporation of the sweat absorbed by the second fabric layer 240 so as to lower the temperature. Therefore, the user is less likely to feel stuffy in an area where the second fabric layer 240 contacts the skin.

Figure 8:
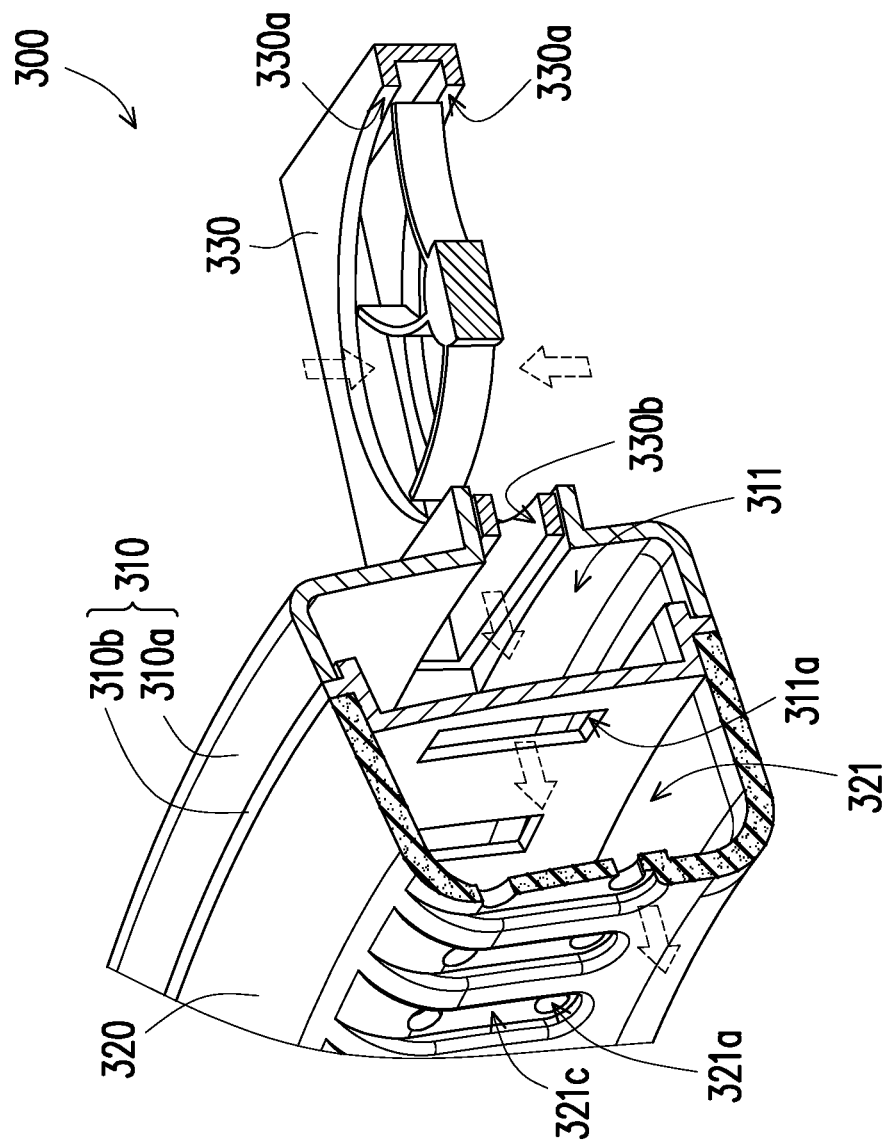
FIG. 8 is a partial cross-sectional view of the third cushion module of FIG. 6A cut along an outlet of a third rear channel.

Referring to FIGS. 6A, 6B, 7A, 7B, 8, and 9, in this embodiment, the third cushion module 300 may include a third hard member 310, a third soft member 320, and multiple third fans 330. The third hard member 310 is connected to the wearable assembly 14 (as shown in FIGS. 1A and 1B). The third soft member 320 is connected to the third hard member 310 to contact a skin 20 (as shown in FIG. 8) of the user, and has a third rear channel 321. The third fans 330 communicate with the third rear channel 321 to introduce the external air into the third rear channel 321.

In this embodiment, the third hard member 310 has a front channel 311, and the third fans 330 communicate with the third rear channel 321 through the front channel 311. The third hard member 310 may include a front cover 310a and a rear cover 310b, and the front cover 310a and the rear cover 310b are connected to each other to form the front channel 311. The third hard member 310 has multiple front channel outlets 311a to communicate the front channel 311 with the third rear channel 321. The third fans 330 may be inserted into the front assembly 12 (as shown in FIGS. 1A and 1B) to inject the external air or the internal air of the front assembly 12 into the third rear channel 321 through the front channel 311. When the internal air of the front assembly 12 is drawn out by the third fan 330, the temperature inside the front assembly 12 may also be lowered.

In this embodiment, the third soft member 320 has one or more third rear channel outlets 321a. The third rear channel outlets 321a communicate with the third rear channel 321 and are located on a surface of the third soft member 320 that contacts the skin of the user. The third soft member 320 has one or more trenches 321c on the surface of the third soft member 320. One or more of the third rear channel outlets 321a are in the corresponding trenches 321c, so that the airflow may flow out from the third rear channel outlets 321a through the trenches 321c. The trenches 321c may be regarded as secondary channels. The third soft member 320 may surround the eyes of the user from a position between eyebrows of the user and extend to cheeks of the user, to abut around the eye sockets of the user. In more detail, since the airflow flows out through the trenches 321c, the user is less likely to feel stuffy in an area where the third soft member 320 contacts the skin.

In this embodiment, the third fans 330 have multiple air inlets 330a and an air outlet 330b. The air inlets 330a respectively communicate with a space enclosed by the front assembly 12 (shown in FIGS. 1A and 1B) and the face of the user and with an external environment, and the air outlet 330b communicates with the third rear channel 321. Therefore, the third fans 330 may draw out the air in the space enclosed by the front assembly 12 (as shown in FIGS. 1A and 1B) and the face of the user and mix the air with air drawn in from the external environment, and then inject the air into the third rear channel 321 and discharge the air to the outside from the third rear channel outlets 321a. Therefore, humidity and temperature in the space enclosed by the front assembly 12 and the face of the user may be further lowered, so that the user is less likely to feel stuffy. Since the air flows out through the trenches 321c, the user is less likely to feel stuffy in an area where the third soft member 320 contacts the skin.

In another embodiment, the air inlets 330a may also simultaneously draw in the high-temperature air in the front assembly 12 and the air in the external environment, and inject the air into the third rear channel 321. Therefore, the temperature inside the front assembly 12 may also be lowered. Since the air flows out through the trenches 321c, the user is less likely to feel stuffy in an area where the third soft member 320 contacts the skin.

Figure 9:
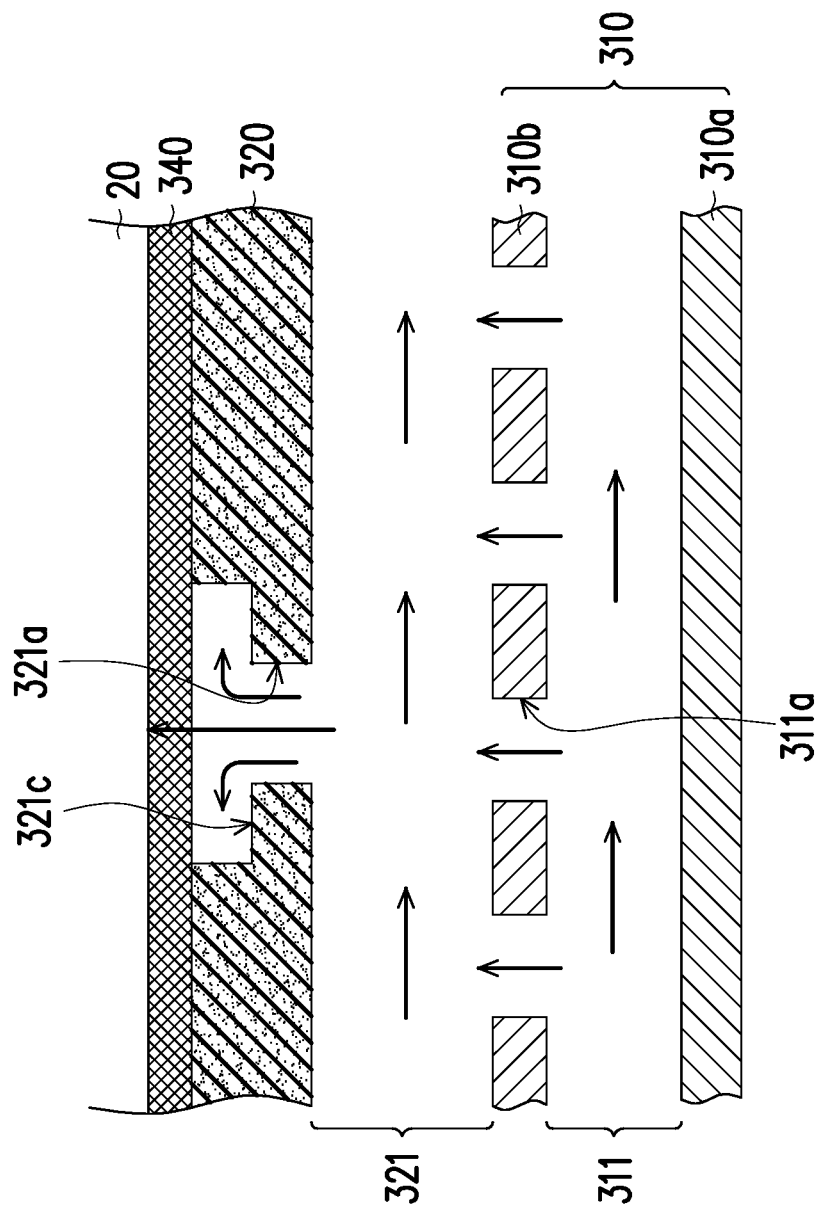
FIG. 9 is a schematic view of an airflow path of the third cushion module of FIG. 6A.

In this embodiment, the third cushion module 300 may further include a third fabric layer 340 (as shown in FIG. 9). The third fabric layer 340 covers the third soft member 320. The third fabric layer 340 may adopt a breathable and cool cloth. The third fabric layer 340 may cover the third soft member 320 in a detachable manner, to be removed for cleaning. In more detail, the airflow flowing out through the trenches 321c facilitates evaporation of the sweat absorbed by the third fabric layer 340 so as to lower the temperature. Therefore, the user is less likely to feel stuffy in an area where the third fabric layer 340 contacts the skin.

Figure 10:
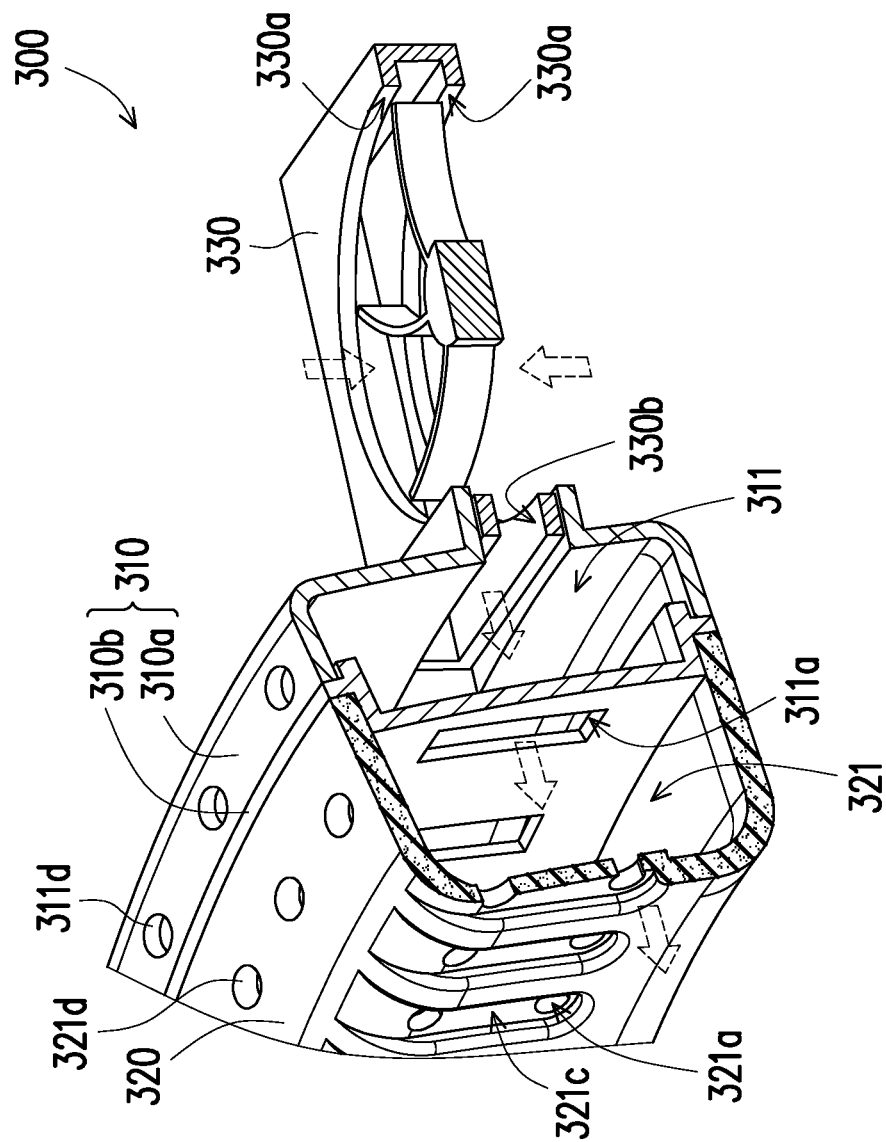
FIG. 10 is a partial cross-sectional view of a third cushion module according to another embodiment of the invention.
Figure 11A:
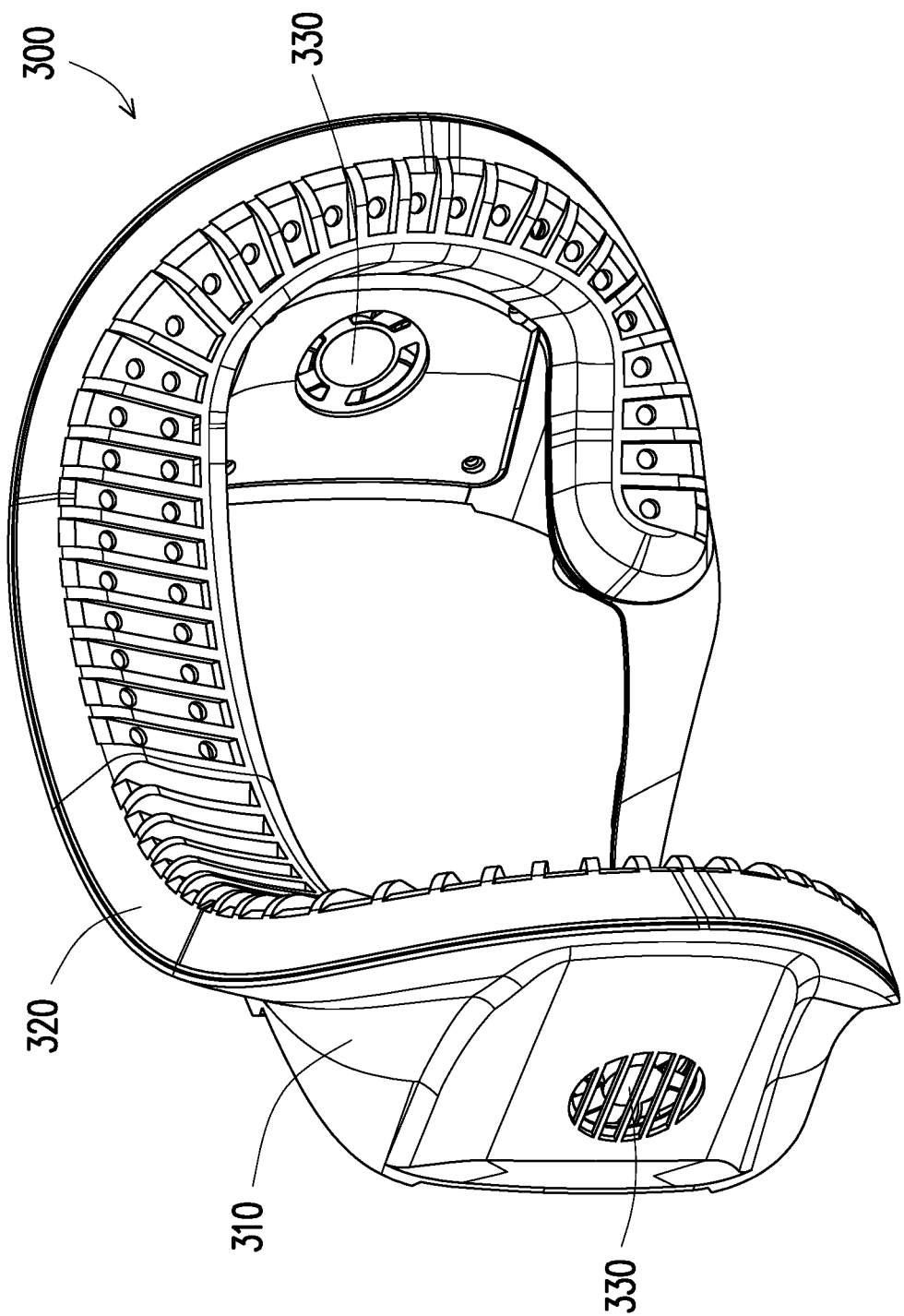
FIG. 11A is a perspective view of a third cushion module according to another embodiment of the invention.
Figure 11B:
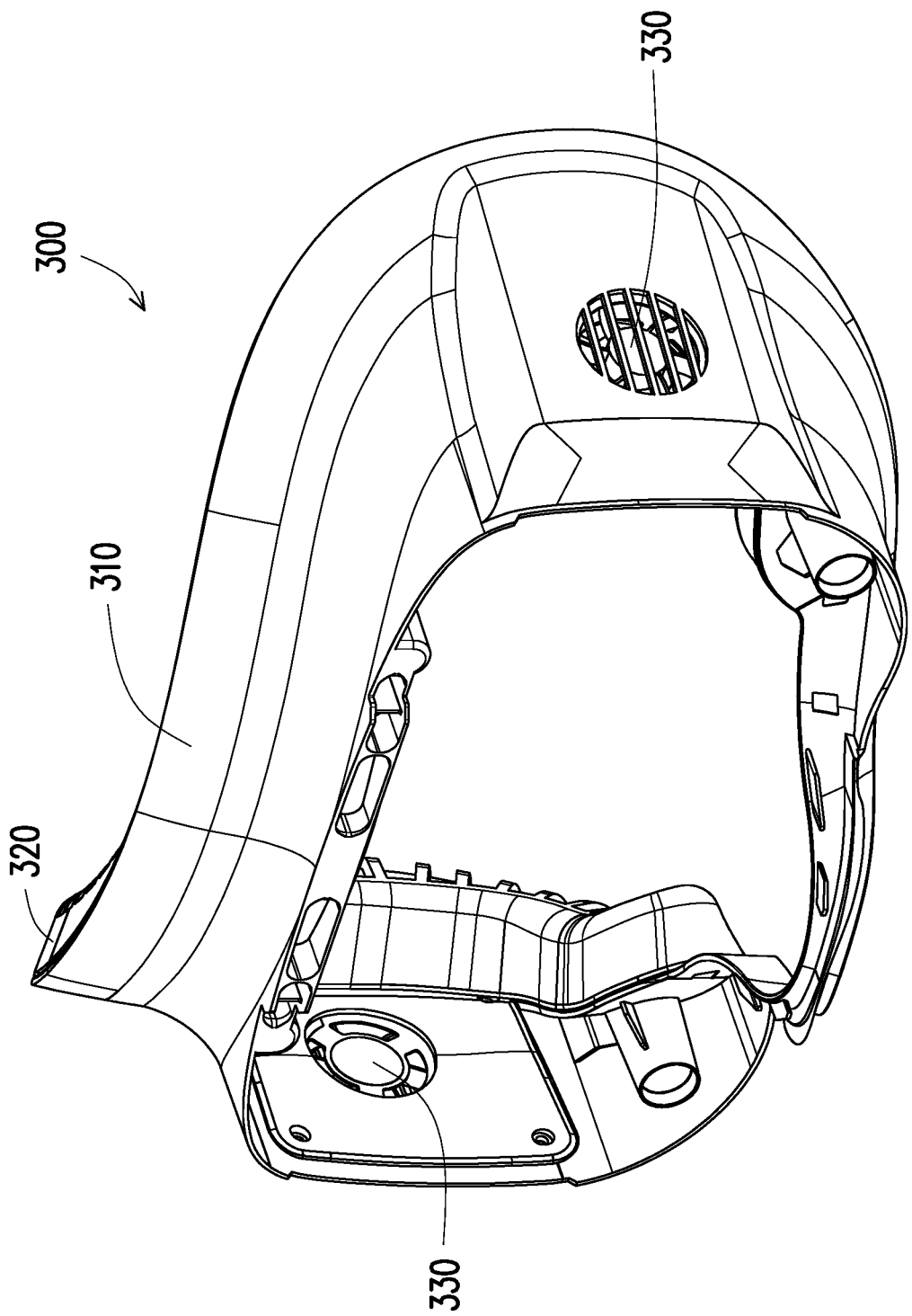
FIG. 11B is a perspective view of the third cushion module of FIG. 11A from another perspective.
Figure 12A:
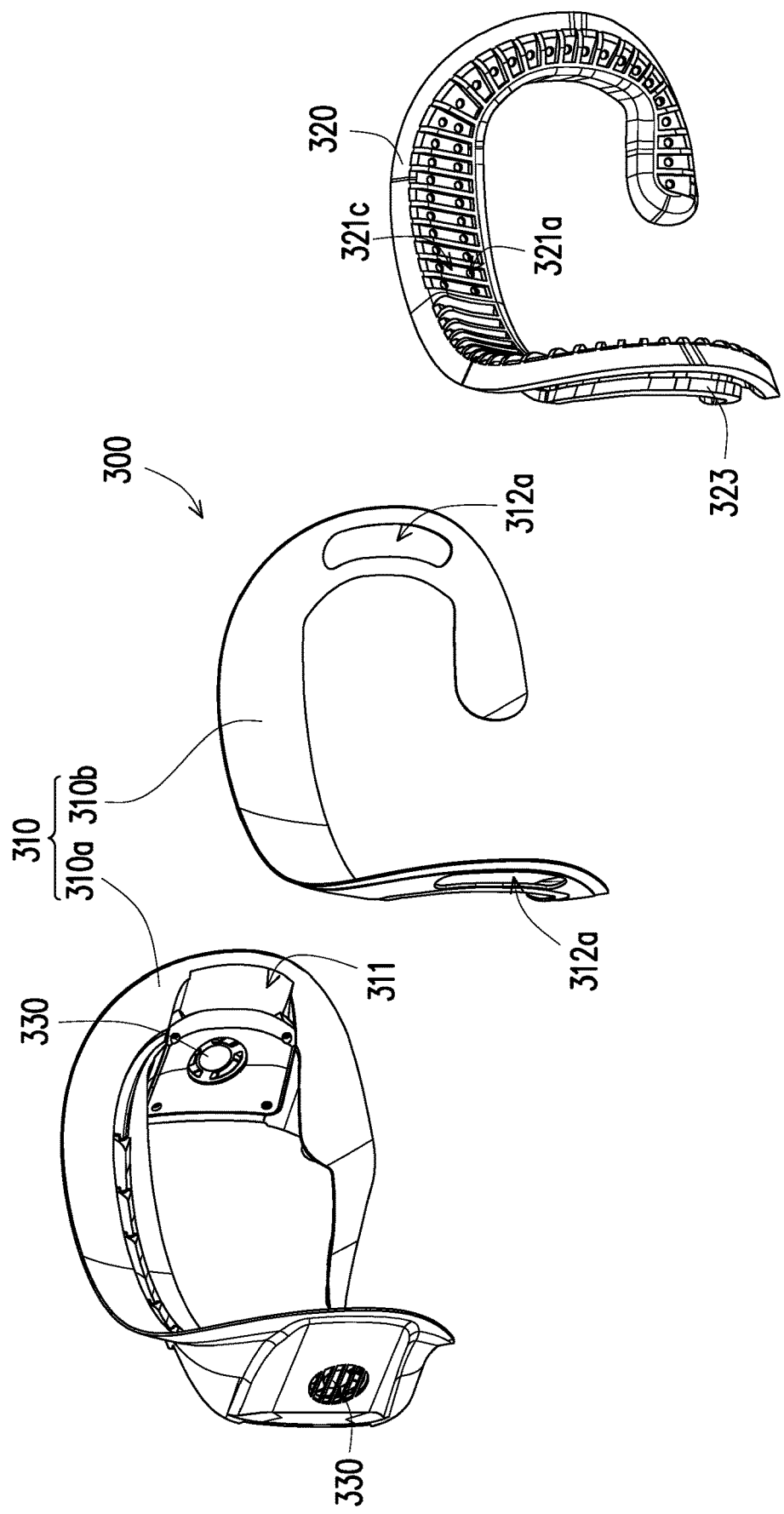
FIG. 12A is an exploded view of the third cushion module of FIG. 11A.
Figure 12B:
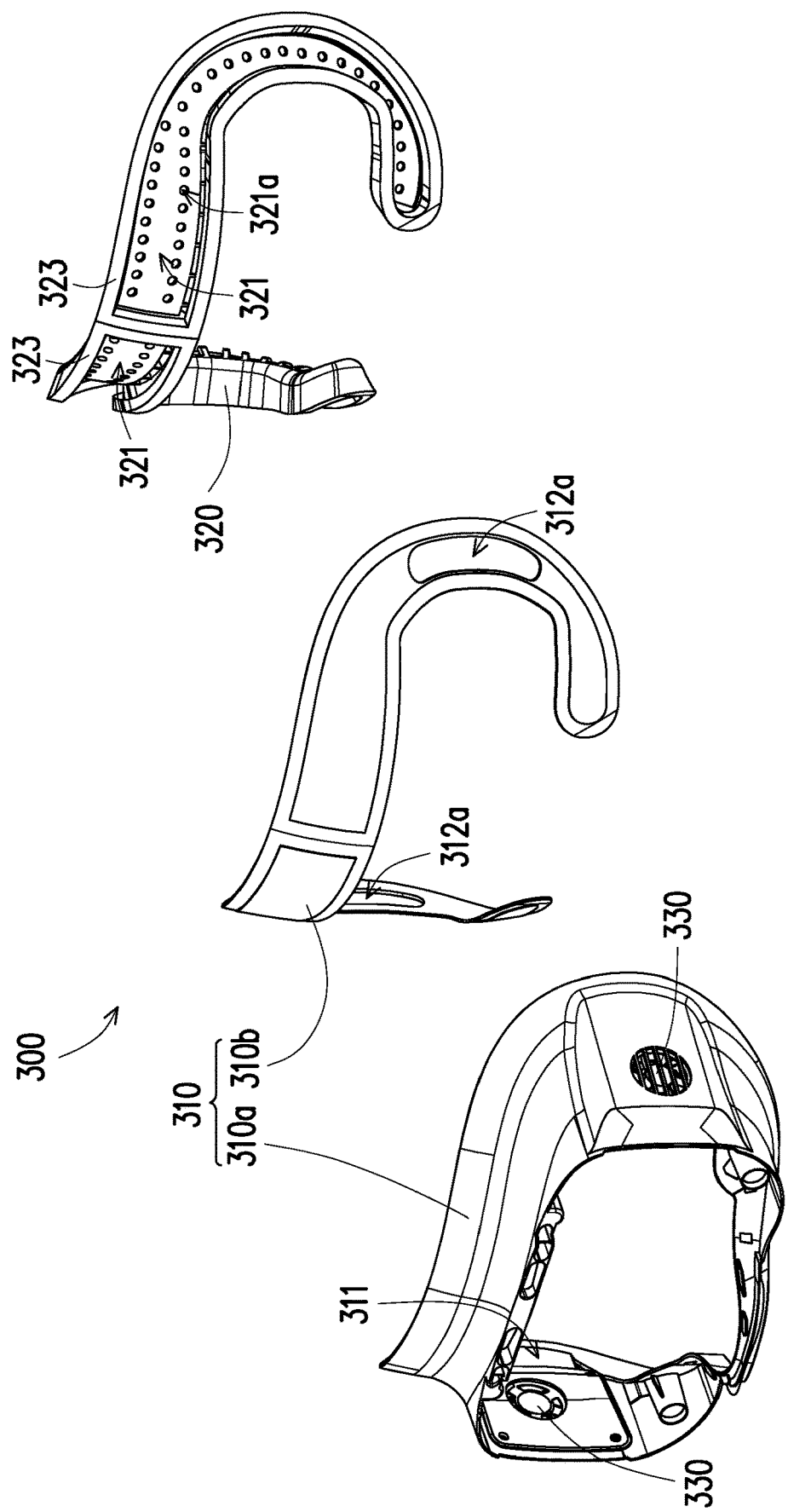
FIG. 12B is an exploded view of the third cushion module of FIG. 11A from another perspective.
Figure 13:
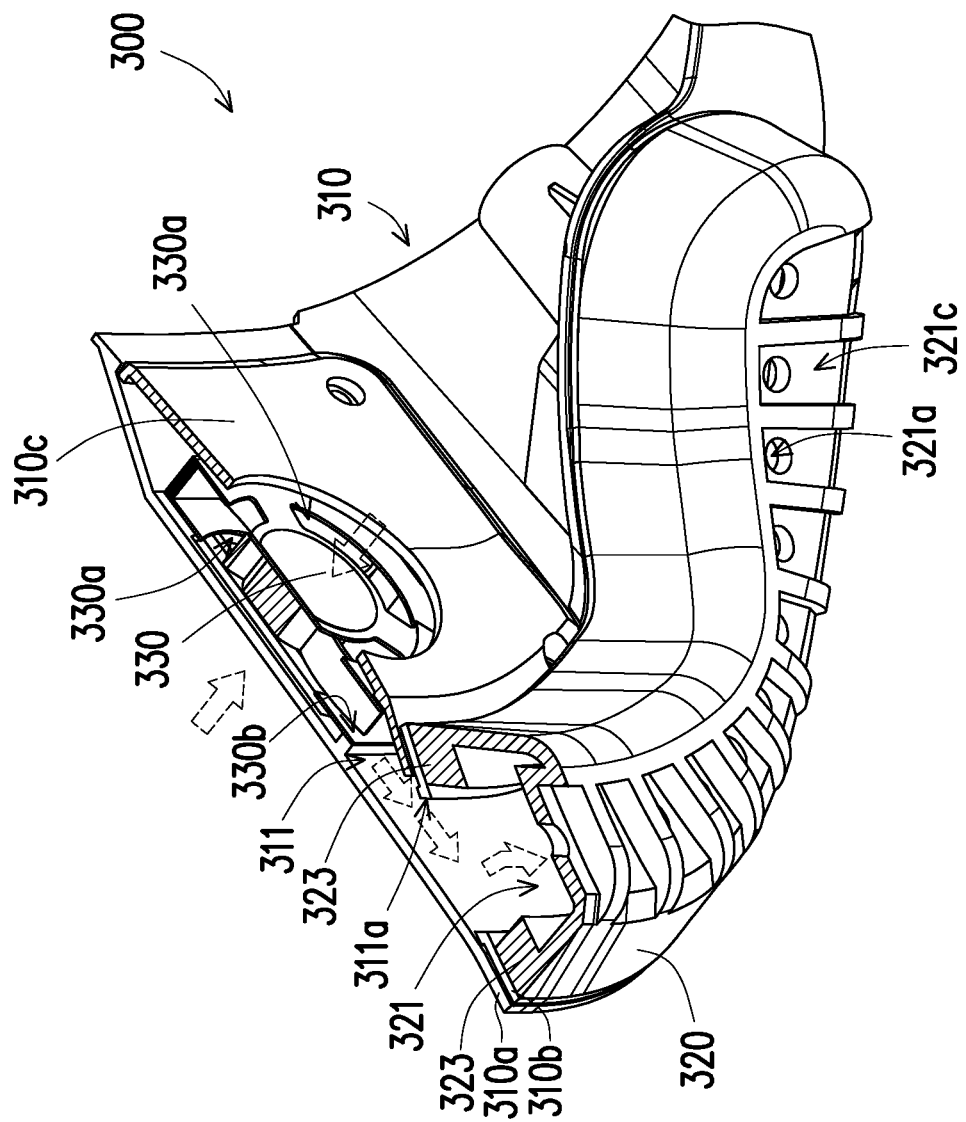
FIG. 13 is a partial cross-sectional view of the third cushion module of FIG. 11A cut along the outlet of the third rear channel.

Referring to FIG. 10, compared with the embodiment of FIG. 8, in another embodiment, the third hard member 310 (such as the front cover 310a of the third hard member 310) may have one or more lateral airflow outlets 311d, and the lateral airflow outlets 311d communicate with the front channel 311. In addition, the third soft member 320 may have one or more lateral rear channel outlets 321d, and the lateral rear channel outlets 321d communicate with the third rear channel 321. The airflow blown from the lateral airflow outlets 311d and the lateral rear channel outlets 321d may flow through an area, such as the forehead, of the face of the user that is not covered by the third soft member 320, so the user may feel cooler.

Figure 6A:
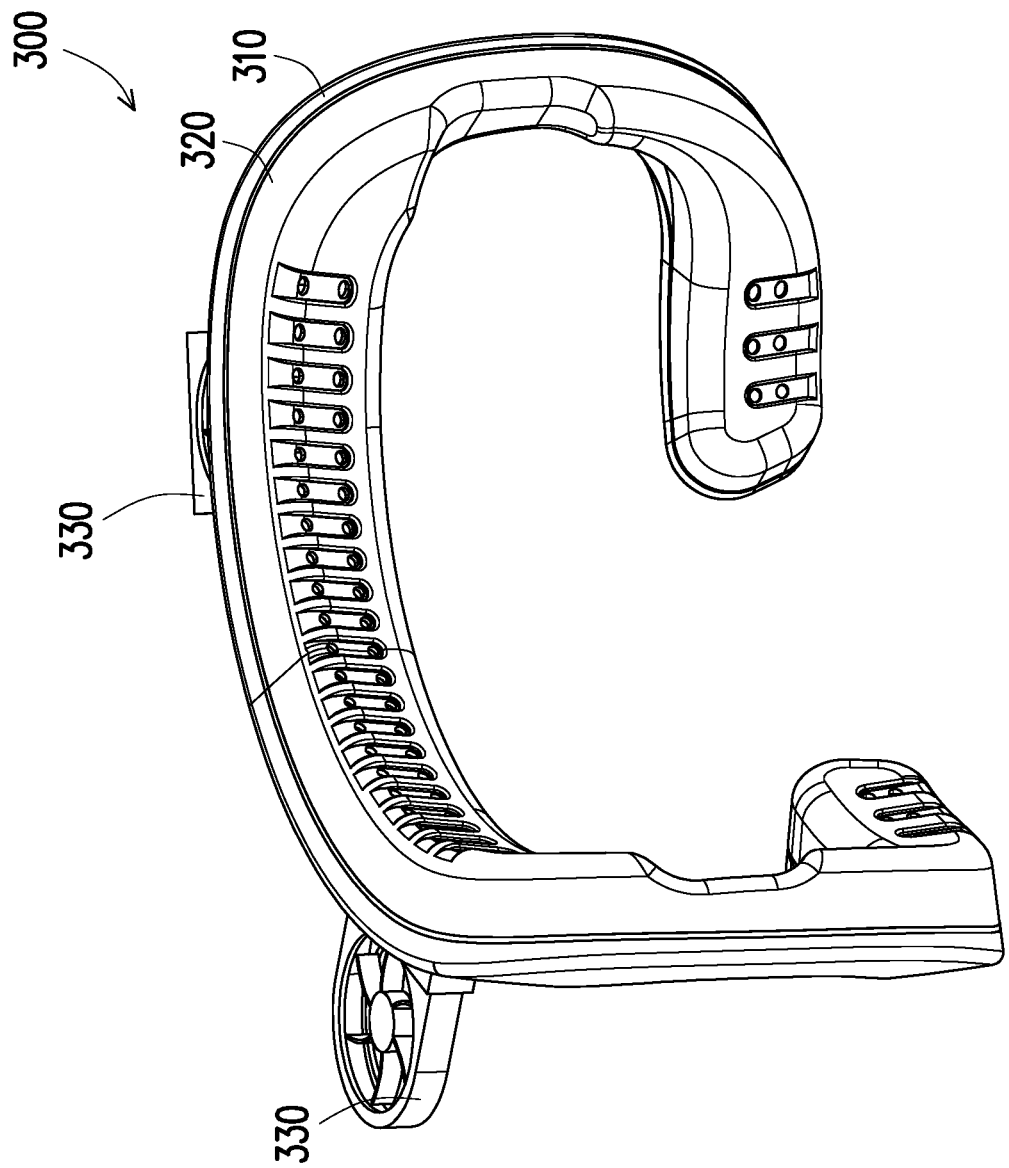
FIG. 6A is a perspective view of a third cushion module of FIG. 1A.
Figure 6B:
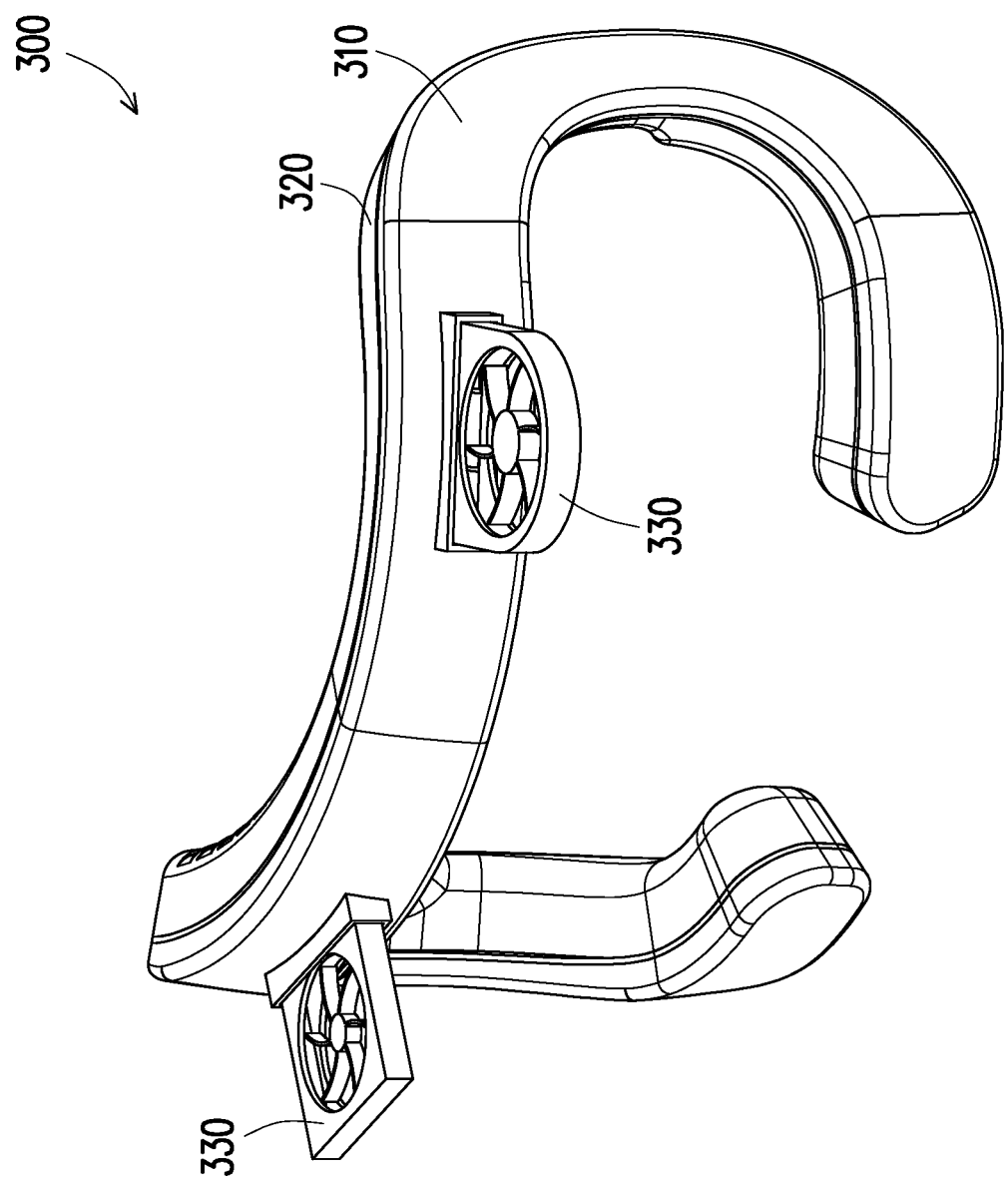
FIG. 6B is a perspective view of the third cushion module of FIG. 6A from another perspective.
Figure 7A:
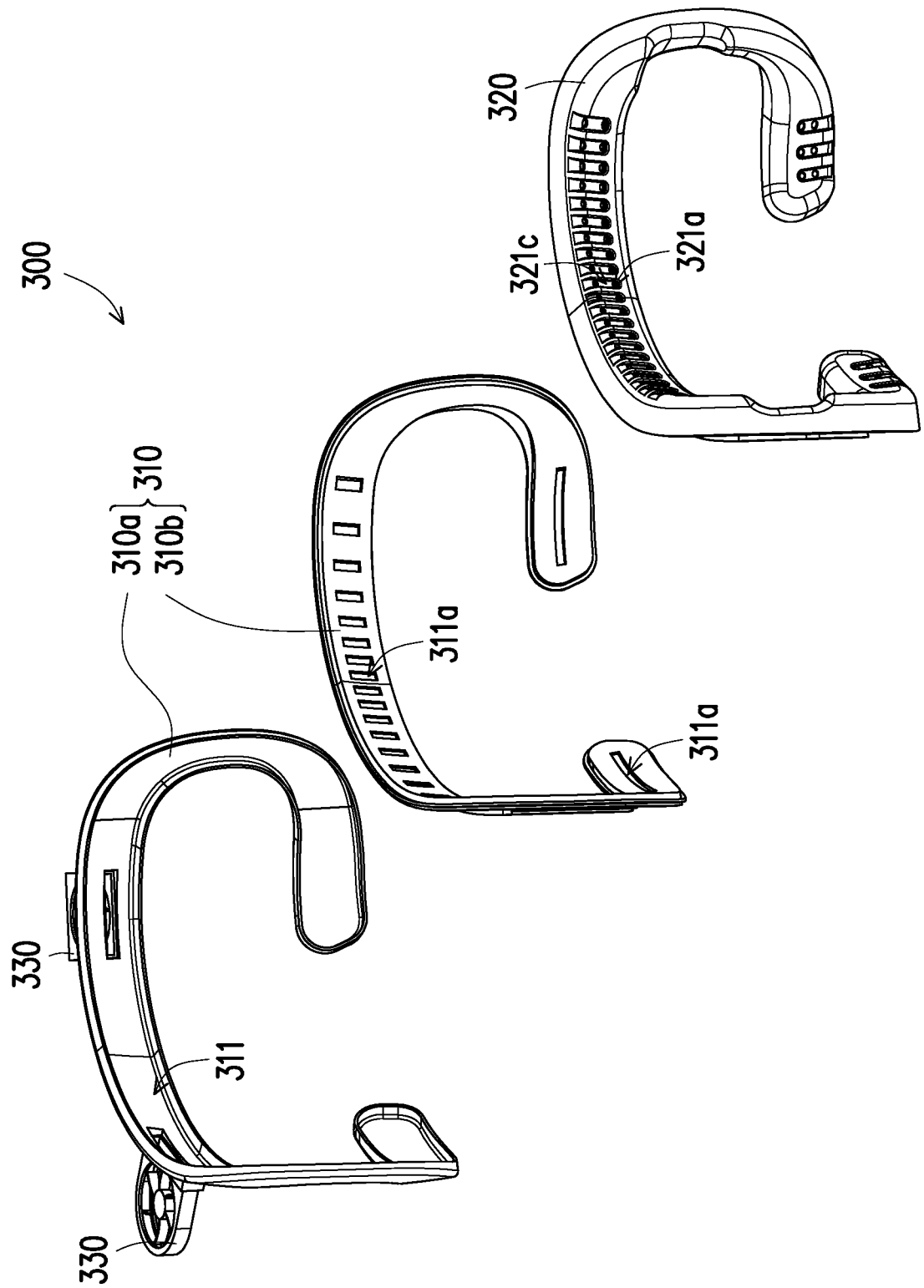
FIG. 7A is an exploded view of the third cushion module of FIG. 6A.
Figure 7B:
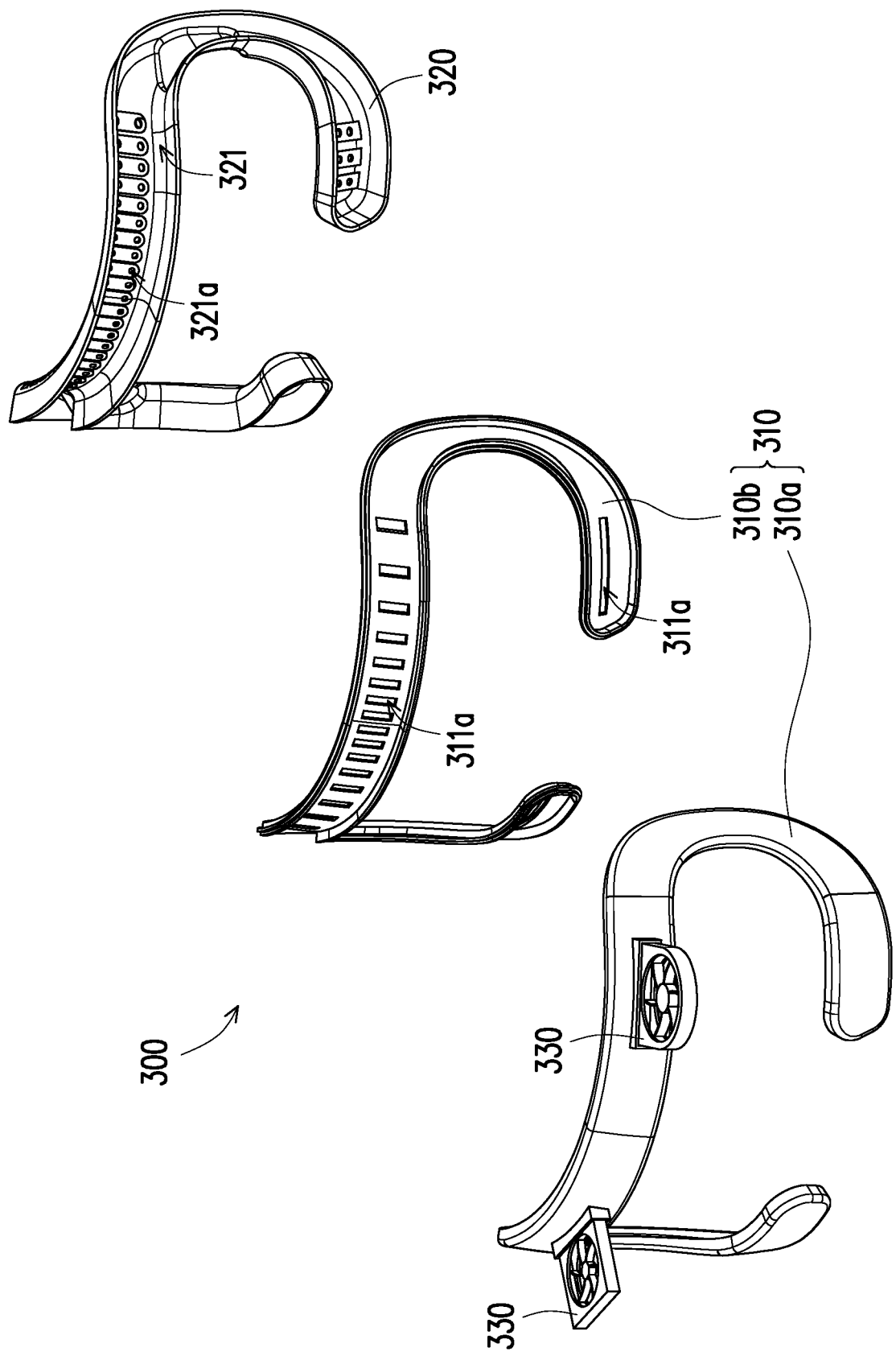
FIG. 7B is an exploded view of the third cushion module of FIG. 6A from another perspective.

Referring to FIGS. 11A, 11B, 12A, 12B, and FIG. 13, another embodiment illustrated therein is substantially the same as the embodiment of FIG. 6A, and the differences between the two embodiments are as follows. First, in the embodiment of FIG. 6A, the third fans 330 are located above the eyes of the user, but in this embodiment, the third fans 330 are respectively located corresponding to the two cheeks of the user, and the third hard member 310 has multiple fan covers 310c, which are fixed to the front cover 310a to fix the third fans 330. In another embodiment, the fan covers 310c may also be integrated into a single member.

In addition, in this embodiment, the third soft member 320 has a thickened portion 323, and the thickened portion 323 is distributed along the third rear channel 321. Therefore, when the third soft member 320 is squeezed or worn, the thickened portion 323 ensures that the third rear channel 321 is not interrupted and remains unblocked as much as possible.

In addition, in this embodiment, the number of the third rear channels 321 is two, and the number of the thickened portions 323 is two. Each of the third rear channels 321 extends from the forehead of the user to the cheeks of the user, and each of the thickened portions 323 is distributed on the outside of the corresponding third rear channel 321. The number of the third fans 330 is two, and the third fans 330 respectively communicate to the third rear channels 321.

The third fans 330 have multiple air inlets 330a and an air outlet 330b. The air inlets 330a respectively communicate with the space enclosed by the front assembly 12 (as shown in FIGS. 1A and 1B) and the face of the user and with the external environment, and the air outlet 330b communicates with the third rear channel 321. Therefore, the third fans 330 may draw out the air in the space enclosed by the front assembly 12 (as shown in FIGS. 1A and 1B) and the face of the user and mix the air with air drawn in from the external environment, and then inject the air into the third rear channel 321 and discharge the air to the outside from the third rear channel outlets 321a. Therefore, humidity and temperature in the space enclosed by the front assembly 12 and the face of the user may be further lowered, so that the user is less likely to feel stuffy. Since the air flows out through the trenches 321c, the user is less likely to feel stuffy in an area where the third soft member 320 contacts the skin.

In this embodiment, the third cushion module 300 may also include a third fabric layer (not shown). The third fabric layer covers the third soft member 320. The third fabric layer may adopt a breathable and cool cloth. The third fabric layer may cover the third soft member 320 in a detachable manner, to be removed for cleaning. In more detail, the airflow flowing out through the trenches 321c facilitates evaporation of the sweat absorbed by the third fabric layer so as to lower the temperature. Therefore, the user is less likely to feel stuffy in an area where the third fabric layer contacts the skin.

Based on the above, the soft member of the cushion module of the head-mounted display device is connected to the hard member and used to contact the skin of the user, and the fan drives the airflow to flow through the rear channel of the soft member to provide a heat dissipation effect.

What is claimed is:

1. A head-mounted display device, comprising: a front assembly;
    a wearable assembly, connected to the front assembly, and adapted for wearing the front assembly onto a face of a user; and
    a cushion module, comprising: a hard member, connected to the wearable assembly or the front assembly;
    a soft member, connected to the hard member to contact skin of the user, and having a rear channel; and
    a fan, communicating with the rear channel and being able to drive airflow to flow through the rear channel to reach and pass through an area where the soft member is in contact with the skin of the user, wherein the fan has a plurality of air inlets and an air outlet, the air inlets respectively communicate with a space enclosed by the front assembly and the face of the user and with an external environment or communicate with an external environment, the air outlet communicates with the rear channel, wherein the hard member comprises a front cover and a rear cover, and the front cover and the rear cover are connected to each other to form the front channel.

2. The head-mounted display device according to claim 1, wherein the hard member has a front channel, and the fan communicates with the rear channel through the front channel.

3. The head-mounted display device according to claim 1, wherein the hard member has at least one front channel outlet, and the at least one front channel outlet communicates the front channel with the rear channel.

4. The head-mounted display device according to claim 1, wherein the soft member has at least one rear channel outlet, and the at least one rear channel outlet communicates with the rear channel and located on a surface of the soft member, which contacts the skin of the user.

5. The head-mounted display device according to claim 1, wherein the soft member has at least one trench on a surface of the soft member, and the at least one rear channel outlet is in the at least one trench.

6. The head-mounted display device according to claim 1, wherein the soft member surrounds eyes of the user from a position between eyebrows of the user and extends to cheeks of the user.

7. The head-mounted display device according to claim 1, wherein the soft member has a thickened portion, and the thickened portion is distributed along the rear channel.

8. The head-mounted display device according to claim 7, wherein a number of the rear channels is two, a number of the thickened portions is two, each of the rear channels extends from a forehead of the user to cheeks of the user, and each of the thickened portions is distributed on an outside of the corresponding rear channel.

9. The head-mounted display device according to claim 8, wherein a number of the fans is two, and the fans respectively communicate to the rear channels.

10. The head-mounted display device according to claim 1, wherein the soft member has a plurality of pillars to abut against a head of the user, and the rear channel extends between the pillars.

11. The head-mounted display device according to claim 1, wherein the cushion module further comprises:
a fabric layer, covering the soft member.

12. The head-mounted display device according to claim 1, wherein the hard member has a front channel, the fan communicates with the rear channel through the front channel, the hard member has at least one lateral airflow outlet, and the at least one lateral airflow outlet communicates with the front channel.

13. The head-mounted display device according to claim 1, wherein the soft member has at least one lateral rear channel outlet, and the at least one lateral rear channel outlet communicates with the rear channel.

* * * * *